US00PP12348P2

(12) United States Plant Patent
Heims

(10) Patent No.: US PP12,348 P2
(45) Date of Patent: Jan. 8, 2002

(54) TIARELLA PLANT NAMED 'BLACK VELVET'

(75) Inventor: Dan M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 09/288,772

(22) Filed: Apr. 8, 1999

(51) Int. Cl.[7] ..... A01H 5/00
(52) U.S. Cl. ..... Plt./263
(58) Field of Search ..... Plt./263

(56) References Cited

U.S. PATENT DOCUMENTS

PP11,168 P * 12/1999 Heims ..... Plt./263

OTHER PUBLICATIONS

UPOV–ROM GTITM Computer Database 2000/04, GTI JOUVE Retrieval Software, citation for "Black Velvet", Aug. 2000.*

Studebaker, Russell "Lower Midwest: sylvan moments" Horticulture v. 97 No. 3, Apr. 2000.*

* cited by examiner

*Primary Examiner*—Howard J. Locker
*Assistant Examiner*—Wendy C Baker
(74) *Attorney, Agent, or Firm*—Klarquist Sparkman, LLP

(57) ABSTRACT

A new and distinct hybrid of Tiarella characterized by its vigor and unique cut leaves of marked coloration and size.

2 Drawing Sheets

The present invention relates to a new and distinct hybrid of Tiarella, which originated as a cross between selected seedlings, Tiarella 'Pinwheel' as the seed parent (unpatented) and Tiarella Seedling 97-63 as the pollen parent (unpatented). Tiarella is in the family Saxifragaceae. Since both parents and the instant plant are interspecific hybrids from several generations of interbreeding and selecting, no species designation is provided.

This new Tiarella is a result of a controlled cross of the aforementioned plants in Canby, Oreg. This hybrid was selected from a large number of seedlings. Parent plants were retained to observe their habit and to compare with the instant plant. The parent plants are neither patented nor commercially available. The new variety has been reproduced only by asexual propagation (division and micropropagation). Each of the progeny exhibits identical characteristics to the original plant.

This plant is characterized by the following:

1. Non-stoloniferous habit.
2. Unique lobed foliage shape.
3. Attractive dark maroon leaf blotching following veins and extending out.
4. Outstanding vigor and leaf-size.

Asexual propagation as done by division and micropropagation, in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTIONS OF THE PHOTOGRAPHS

DETAILED PLANT DESCRIPTION

Figure 1:
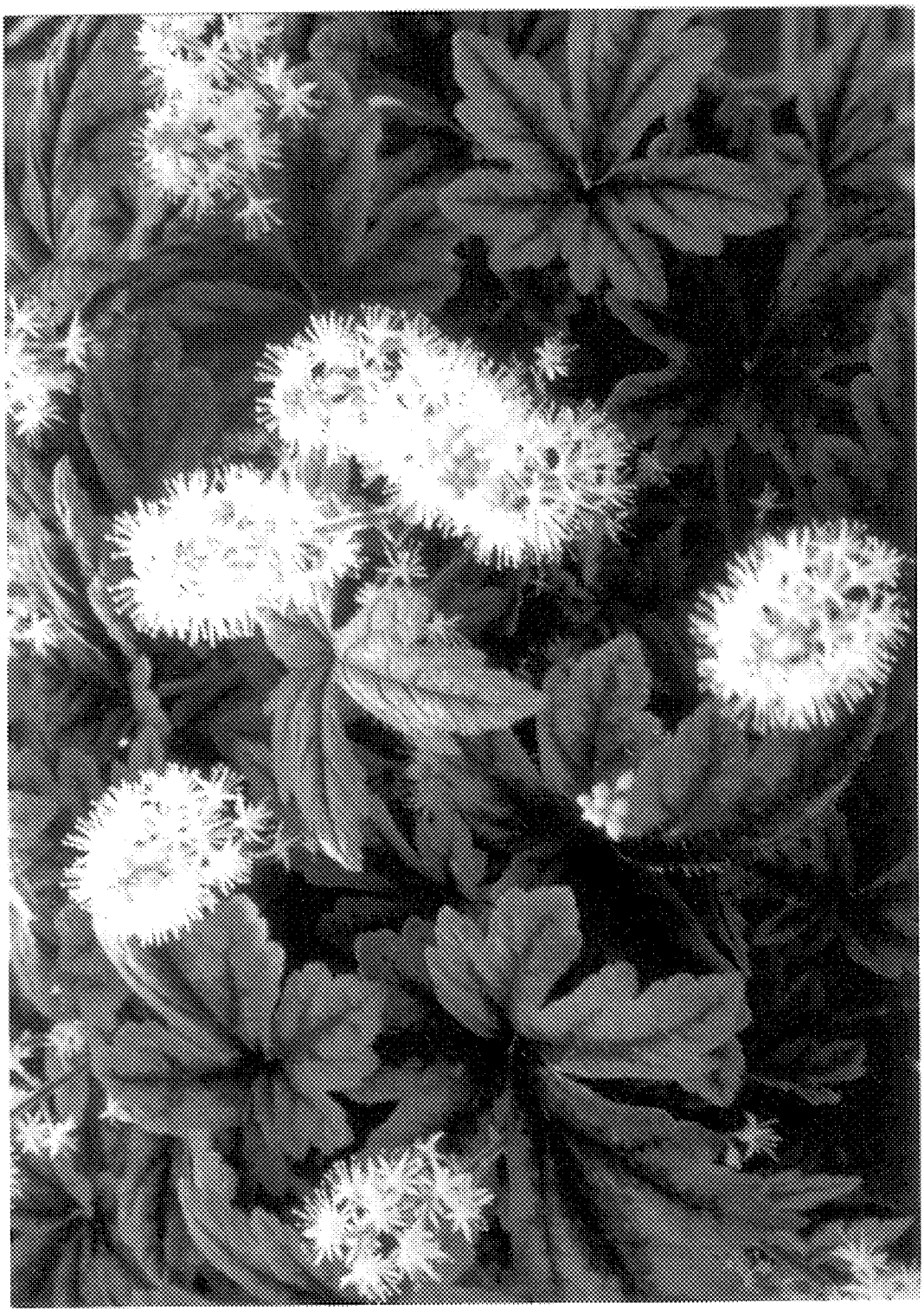
FIG. 1 is a picture of Tiarella 'Black Velvet' in bloom in April in Canby, Oreg.
Figure 2:
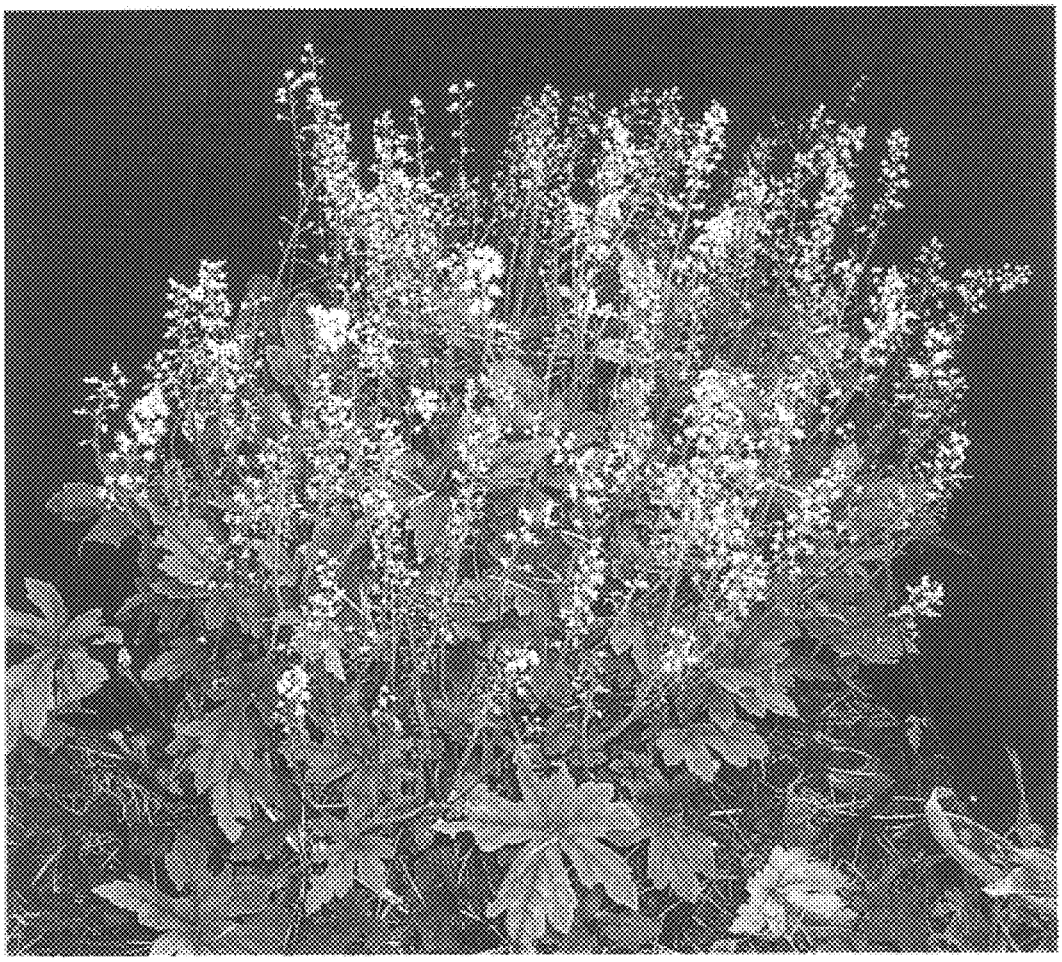
FIG. 2 is an additional view of the plant.

The following is a detailed description of the new Tiarella hybrid based on observations of two-year-old, field grown specimens in Canby, Oreg. The color descriptions are all based on The Royal Horticultural Society Colour Chart.

Plant:

*Type.*—Herbaceous perennial, evergreen in USDA hardiness zone 5 and above and dies down to the ground in zones 3 and 4.

*Form.*—Basal clump.

*Size.*—46 cm. wide and 22–25 cm. to the top of the leaves and 30–35 cm. to the top of the flowers on two-year-old plants.

Foliage:

*Type.*—Simple.

*Shape.*—Ovate. Leaves are "cupped" convexly to 1 cm in depth.

*Margins.*—Palmately 3 to 5-parted, the center lobe is up to twice as wide as the other lobes, giving it an oak leaf appearance. Irregularly serrate with scabrous hairs.

*Venation.*—Palmate.

*Apex.*—Acute to apiculate.

*Base.*—Cordate.

*Length.*—6–7.5 cm.

*Width.*—7–8.5 cm.

*Petiole length.*—12–14.5 cm.

*Base.*—Cordate.

*Aspect.*—Matte.

*Surface.*—Hispid, on the top and bottom surfaces with bottom hairs shorter, giving the leaf a rough texture.

Inflorescence:

*Type.*—Raceme to 30–35 cm, with one or two leaves on the flowering stem. There may be up to 60–75 racemes at one time on a two-year-old plant in Canby, Oreg. Raceme may branch once or twice, extending the bloom time.

*Flower number.*—40–50 blooms per raceme.

*Bloom period.*—April to May. Minor sporadic rebloom in October to November in Canby, Oreg. Individual racemes are in color for 10 days.

Flower:

*Type.*—Perfect, actinomorphic.

*Shape.*—Rotate, star-shaped, outfacing. Petals and sepals similar in color and size.

*Petal and sepal number.*—5 petals, 5 sepals.

*Flower size.*—0.50 cm wide and long.

*Petal shape.*—Elliptic with a clawed base.

*Petal size.*—0.4 cm long, slightly longer than the sepals.

*Calyx.*—Campanulate, parted almost to the base.

*Bud.*—Small, downfacing, ovoid shaped, light pink, puberulent.

*Stamens.*—10, filaments white, 0.05 cm long.

*Pollen.*—RHS Greyed-Orange Group 167B.

*Pistil.*—1, white, 0.35 cm long.

*Fragrance.*—Slight spicy fragrance is noted.

*Fertility.*—Tiarella 'Black Velvet' is fertile.

*Stem.*—To about 30 cm long by about 1.5 mm wide. Puberulent. No tendency towards fasciation observed.

Fruit: A one-celled capsule, beak-like, composed of 2 unequal parts.

Seeds: Few.

Disease resistance: This new hybrid shows good mildew tolerance, the main problem for Tiarella.

Color characteristics:

Foliage:

*Leaf centers.*—Deep maroon, RHS 187A Greyed Purple Group, along each lobe's central vein, major lateral veins, and the leaf center.

*Spring/summer upper surface.*—Note: Two colors of green may be visible on the leaves of the same plant in spring. Coloration is dependent on the maturity of the leaf. Mature leaves show the color RHS 147B Yellow-Green group) and young leaves are RHS 137B Green Group.

*Spring/summer lower surface.*—RHS 147C Yellow-Green Group.

*Spring/summer new growth.*—RHS 137B Green Group.

*Winter color upper surface.*—RHS 147B Yellow-Green Group to RHS Brown Group 200A–D and some Greyed-Orange 177A.

Flowers: RHS 155C White Group, shading from RHS 36C Red Group. Buds are 36B–C Red Group.

*Flower stems.*—RHS 199A Grey-Brown group with some maroon.

DESCRIPTION OF PARENT PLANTS

This Tiarella hybrid has characteristics which make it unique from its parents. Compared to its seed parent, Tiarella 'Pinwheel', this new hybrid has darker markings, greater vigor, and a different leaf shape. Compared to its pollen parent, Tiarella Seedling 97-63, this new hybrid has lighter colored flowers, darker markings, and a different leaf shape. Tiarella Seedling 97-67 is an extremely vigorous plant with large, pink tinted flowers, and moderate markings and Tiarella 'Pinwheel' has lightly marked foliage, and broad, cut leaves which overlap 5 percent of the leaflet's width.

Compared with Tiarella 'Ninja' (U.S. Plant Pat. No. 11,168), Tiarella 'Black Velvet' is more vigorous, with lighter pink flowers, and broader leaf lobes giving the leaf a more oak leaf look.

I claim:

1. A new and distinct hybrid of Tiarella plant substantially as shown and described, characterized by its vigor and unique cut leaves of marked coloration and size.

* * * * *